US010451578B2

(12) United States Patent
Cai et al.

(10) Patent No.: US 10,451,578 B2
(45) Date of Patent: Oct. 22, 2019

(54) METHOD FOR DISTINGUISHING BETWEEN QUALITY CONTROL LIQUID AND REAL SAMPLE IN AN ELECTROCHEMICAL TEST SYSTEM WITH RECOGNITION DEVICE CONTROLLER AND RECOGNITION SYSTEM

(71) Applicant: Sinocare Inc., Changsha (CN)

(72) Inventors: Xiaohua Cai, Changsha (CN); Zhao Huang, Changsha (CN)

(73) Assignee: Sinocare Inc., Changsha (CN)

( * ) Notice: Subject to any disclaimer, the term of this patent is extended or adjusted under 35 U.S.C. 154(b) by 93 days.

(21) Appl. No.: 15/498,167

(22) Filed: Apr. 26, 2017

(65) Prior Publication Data
US 2018/0172617 A1    Jun. 21, 2018

(30) Foreign Application Priority Data
Dec. 21, 2016 (CN) .......................... 2016 1 1193205

(51) Int. Cl.
*G01N 27/327* (2006.01)
*C12Q 1/00* (2006.01)
*G01N 33/49* (2006.01)

(52) U.S. Cl.
CPC ......... *G01N 27/3274* (2013.01); *C12Q 1/001* (2013.01); *G01N 27/3272* (2013.01); *G01N 33/49* (2013.01)

(58) Field of Classification Search
CPC .......................................... G01N 27/327–3274
See application file for complete search history.

(56) References Cited

U.S. PATENT DOCUMENTS

| | | | |
|---|---|---|---|
| 7,966,859 B2* | 6/2011 | Wu | G01N 35/00029 73/1.02 |
| 9,408,567 B2 | 8/2016 | Wang et al. | |
| 2003/0064525 A1* | 4/2003 | Liess | G01N 27/3274 436/149 |
| 2010/0264942 A1 | 10/2010 | Okami et al. | |

(Continued)

FOREIGN PATENT DOCUMENTS

CN         205263094 U        5/2016

*Primary Examiner* — J. Christopher Ball
(74) *Attorney, Agent, or Firm* — Lambert Shortell & Connaughton; Gary E. Lambert; David J. Connaughton, Jr.

(57) ABSTRACT

The present invention relates to the technical field of electrochemical detection, in particularly to a method for distinguishing between quality control liquid and real sample in an electrochemical test system with recognition device controller and recognition system. The method includes: (1) applying an AC voltage signal to the electrode surface(s) of an electrochemical test strip, (2) measuring the AC impedance angle (phase angle) value between working electrode and reference electrode after drawing a test sample into the fluid chamber of an electrochemical test strip, (3) automatically judging the test sample as quality control liquid or real sample according to the AC impedance angle value. The method provided by the invention can automatically distinguish between quality control liquid and real sample in an electrochemical test system, simplifying the operation steps of quality control, avoiding the misoperation under manual quality control mode, and improving the accuracy and reliability of measurement results.

18 Claims, 5 Drawing Sheets

(56) References Cited

U.S. PATENT DOCUMENTS

2011/0208435 A1* 8/2011 Elder .................. G01N 27/307
                                                                    702/19
2016/0146750 A1   5/2016 Hughes et al.

* cited by examiner

METHOD FOR DISTINGUISHING BETWEEN QUALITY CONTROL LIQUID AND REAL SAMPLE IN AN ELECTROCHEMICAL TEST SYSTEM WITH RECOGNITION DEVICE CONTROLLER AND RECOGNITION SYSTEM

FILED OF THE INVENTION

The present invention relates to the technical field of electrochemical detection, in particular to a method for distinguishing between quality control liquid and real sample in an electrochemical test system with recognition device controller and recognition system.

BACKGROUND OF THE INVENTION

Electrochemical test systems based on the principle of electrochemical biosensor are widely used in the field of point-care-of-testing (POCT). Usually, electrochemical test systems comprise an electrochemical test strip and an electrochemical instrument. The biological molecules (such as enzyme) modified on the electrode of test strip can selectively identify the target analytes of the test sample, and the biorecognition signals are transformed into electrical signals (e.g., oxidation or reduction current) during this process. Then the electrochemical instrument can collect and measure the electrical signals to quantitatively detect the target analytes. Electrochemical test systems of this type can be used to detect a variety of disease markers in the blood, and is of significance to the prevention and adjuvant treatment for related diseases.

Generally, in order to ensure the reliability and accuracy of an electrochemical test system, quality control of such a system should be carried out regularly to determine whether the test system can work properly. For instance, the common blood glucose test system is equipped with blood glucose quality control liquid, the operator needs to measure blood glucose quality control liquid on blood glucose test system at regular intervals. If the measured value exceeds the concentration range of blood glucose quality control liquid, the result indicates the reduced reliability of blood glucose test system, thus the blood glucose test system can not be used for clinical detection.

The common quality control mode of electrochemical test system for an operator is to manually select the quality control measurement mode on the test system, then installing an electrochemical test strip in the electrochemical instrument. Quality control measurement can be achieved by supplying quality control liquid to the electrochemical test strip. In this mode of operation, the operator will need to manually switch measurement mode between quality control measurement and real sample (such as blood) measurement. If the operator measures the real sample on the test system under the quality control measurement mode, or measures the quality control liquid on the test system under the real sample measurement mode, it will give a risk of inaccurate test results, and can not guide the operator to make a correctly clinical judgment. So it is highly desirable to develop a method to automatically distinguish between quality control liquid and real sample in an electrochemical test system, which is of great significance to simplify the operation steps of quality control, avoid the misoperation under manual quality control mode, and improve the accuracy and reliability of measurement results.

SUMMARY OF THE INVENTION

Accordingly, the presented invention provides a method for distinguishing between quality control liquid and real sample in an electrochemical test system with recognition device controller and recognition system. The method can accurately distinguish between quality control liquid and real sample such as blood.

In a first aspect, a method is provided for distinguishing between quality control liquid and real sample in an electrochemical test system. The method comprises applying an AC voltage signal to the electrode surface(s) of an electrochemical test strip, measuring the AC impedance angle value (i.e. phase difference between phase voltage and phase current in AC circuit) between work electrode and reference electrode after drawing test sample into the fluid chamber of electrochemical test strip, and automatically judging the test sample as quality control liquid or real sample according to the AC impedance angle value.

In an embodiment of the first aspect, the real sample is the test sample except the quality control liquid.

In an embodiment of the first aspect, the real sample is blood in the examples provided by the invention.

In an embodiment of the first aspect, the process for judging the test sample as quality control liquid or real sample according to the AC impedance angle value includes: selecting the AC impedance angle threshold on the electrochemical test system based on the type of the test strip, comparing the measured AC impedance angle value of the test sample with the AC impedance angle threshold, judging the test sample as quality control liquid or real sample from the comparison result.

In an embodiment of the first aspect, the process for selecting the AC impedance angle threshold on the electrochemical test system based on the type of the test strip includes: identifying the code of test strip by electrochemical instrument, determining the test strip as the first type or second type, reading the corresponding AC impedance angle threshold from the storage area according to the type of test strip.

In an embodiment of the first aspect, the AC impedance angle threshold is determined to threshold A for the first type of test strip, the judgment method is: (1) when the measured AC impedance angle value of the test sample is larger than the threshold A, the test sample is judged as quality control liquid; (2) when the measured AC impedance angle value of the test sample is smaller than the threshold A, the test sample is judged as real sample.

In an embodiment of the first aspect, the AC impedance angle threshold is determined to threshold B for the second type of test strip, the judgment method is: (1) when the measured AC impedance angle value of the test sample is smaller than the threshold B, the test sample is judged as quality control liquid; (2) when the measured AC impedance angle value of the test sample is larger than the threshold B, the test sample is judged as real sample.

In an embodiment of the first aspect, the process for determining the AC impedance angle threshold of the first type of test strip includes: making a number of real samples corresponding to the first type of test strip, using the first type of test strip to measure the AC impedance angle values of multiple real samples, and taking the maximum value of 130%~140% as the AC impedance angle threshold.

In an embodiment of the first aspect, the process for determining the AC impedance angle threshold of the second type of test strip includes: making a number of real samples corresponding to the second type of test strip, using the second type of test strip to measure the AC impedance angle values of multiple real samples, and taking the minimum value of 55%~65% as the AC impedance angle threshold.

In an embodiment of the first aspect, the process for determining the AC impedance angle threshold of the first type of test strip includes: making a number of quality control liquid samples corresponding to the first type of test strip, using the first type of test strip to measure the AC impedance angle values of multiple quality control liquid samples, and taking the minimum value of 80%~85% as the AC impedance angle threshold.

In an embodiment of the first aspect, the process for determining the AC impedance angle threshold of the second type of test strip includes: making a number of quality control liquid samples corresponding to the second type of test strip, using the second type of test strip to measure the AC impedance angle values of multiple quality control liquid samples, and taking the maximum value of 200%~225% as the AC impedance angle threshold.

In a second aspect, the presented invention provides a recognition device controller to distinguish between quality control liquid and real sample in an electrochemical test system, the recognition device controller includes an AC impedance angle value acquisition module and a judging module. Each module may be a computerized routine controlled by a computer controller, or may be a standalone computerized unit or device.

In an embodiment of the second aspect, the recognition device controller includes an AC impedance angle threshold acquisition module.

In an embodiment of the second aspect, the working routine for AC impedance angle value acquisition module comprises applying an AC voltage signal to the electrode surface(s) of an electrochemical test strip, and measuring the AC impedance angle value between work electrode and reference electrode after drawing test sample into the fluid chamber of electrochemical test strip.

In an embodiment of the second aspect, the working routine for judging module includes judging the test sample as quality control liquid or real sample according to the AC impedance angle value provided by the AC impedance angle value acquisition module.

In an embodiment of the second aspect, the process for judging the test sample as quality control liquid or real sample according to the AC impedance angle value includes: selecting the AC impedance angle threshold on the electrochemical test system based on the type of the test strip, comparing the measured AC impedance angle values of the test sample with the AC impedance angle threshold, and judging the test sample as quality control liquid or real sample from the comparison result.

In an embodiment of the second aspect, the process for selecting the AC impedance angle threshold on the electrochemical test system based on the type of the test strip includes: identifying the code of test strip by electrochemical instrument, determining the test strip as the first type or second type, and reading the corresponding AC impedance angle threshold from the storage area (such as a computer memory) according to the type of test strip.

In an embodiment of the second aspect, the AC impedance angle threshold is determined to threshold A for the first type of test strip, the judgment method is: (1) when the measured AC impedance angle value of the test sample is larger than the threshold A, the test sample is judged as quality control liquid; (2) when the measured AC impedance angle value of the test sample is smaller than the threshold A, the test sample is judged as real sample.

In an embodiment of the second aspect, the AC impedance angle threshold is determined to threshold B for the second type of test strip, the judgment method is: (1) when the measured AC impedance angle value of the test sample is smaller than the threshold B, the test sample is judged as quality control liquid; (2) when the measured AC impedance angle value of the test sample is larger than the threshold B, the test sample is judged as real sample.

In an embodiment of the second aspect, the process for determining the AC impedance angle threshold of the first type of test strip includes: making a number of real samples corresponding to the first type of test strip, using the first type of test strip to measure the AC impedance angle values of multiple real samples, taking the maximum value of 130%~140% as the AC impedance angle threshold.

In an embodiment of the second aspect, the process for determining the AC impedance angle threshold of the second type of test strip includes: making a number of real samples corresponding to the second type of test strip, using the second type of test strip to measure the AC impedance angle values of multiple real samples, taking the minimum value of 55%~65% as the AC impedance angle threshold.

In an embodiment of the second aspect, the process for determining the AC impedance angle threshold of the first type of test strip includes: making a number of quality control liquid samples corresponding to the first type of test strip, using the first type of test strip to measure the AC impedance angle values of multiple quality control liquid samples, taking the minimum value of 80%~85% as the AC impedance angle threshold.

In an embodiment of the second aspect, the process for determining the AC impedance angle threshold of the second type of test strip includes: making a number of quality control liquid samples corresponding to the second type of test strip, using the second type of test strip to measure the AC impedance angle values of multiple quality control liquid samples, taking the maximum value of 200%~225% as the AC impedance angle threshold.

In a third aspect, the presented invention provides a recognition system to distinguish between quality control liquid and real sample in an electrochemical test system, the recognition system includes recognition device controller, AC impedance angle value detection device and type of test strip identification module.

In an embodiment of the third aspect, recognition system includes threshold storage module. As noted, each module may be a computerized routine controlled by a computer controller, or may be a standalone computerized unit or device.

The presented invention provides a method for distinguishing between quality control liquid and real sample in an electrochemical test system. The method comprises applying an AC voltage signal to the electrode surface (or electrode surfaces depending on embodiment) of an electrochemical test strip, measuring the AC impedance angle value between work electrode and reference electrode after drawing test sample into the fluid chamber of electrochemical test strip, automatically judging the test sample as quality control liquid or real sample according to the AC impedance angle value.

The method provided in the invention can automatically distinguish between quality control liquid and real sample in an electrochemical test system, which is beneficial to simplify the operation steps of quality control, avoid the misoperation under manual quality control mode, and improve the accuracy and reliability of measurement results.

DETAILED DESCRIPTION OF THE PREFERRED EMBODIMENT

The presented invention provides a system, method, and related device(s) for distinguishing between quality control liquid and real sample in an electrochemical test system with recognition device controller and recognition system. This allows for accurate distinction between quality control liquid and real sample such as blood.

The method provided in the invention comprises applying an AC voltage signal to the electrode surface(s) of an electrochemical test strip, measuring the AC impedance angle value (i.e. phase difference between phase voltage and phase current in AC circuit) between work electrode and reference electrode after drawing test sample into the fluid chamber of electrochemical test strip, and automatically judging the test sample as quality control liquid or real sample according to the AC impedance angle value.

The real sample is the test sample except the quality control liquid in the invention.

The real sample may be blood in the embodiments provided by the invention.

In one embodiment provided by the invention, the electrochemical test system is blood glucose electrochemical test system, the real sample is blood; the process for judging the test sample as quality control liquid or real sample according to the AC impedance angle value includes: selecting an AC impedance angle threshold A to distinguish between the real sample and quality control liquid, and the threshold A is set as the 130%~140% of maximum value of AC impedance angle value for real sample, or the 80%~85% of minimum value of AC impedance angle value for quality control liquid;

When the measured AC impedance angle value of the test sample is smaller than the threshold A, the test sample is judged as blood sample, when the measured AC impedance angle value of the test sample is larger than the threshold A, the test sample is judged as quality control liquid.

The blood glucose quality control liquid is composed of thickener, preservative, glucose, electrolyte and buffer. In one embodiment, the concentration of electrolyte is 300~700 mM. In a particular embodiment, preferably, the concentration of electrolyte is 500 mM.

In one embodiment, the blood glucose quality control liquid is composed of polyethylene glycol 10000, $NaN_3$, glucose, NaCl and 0.1 M phosphate buffer (pH=7.0). The concentration of NaCl may be 300~700 mM, and in particular may be 500 mM.

In another preferred embodiment, the compositions of blood glucose quality control liquid include: 4 g polyethylene glycol 10000, 0.0003 g $NaN_3$, 200 mg/dL glucose, 300~700 mM NaCl, 100 mL 0.1 M phosphate buffer (pH=7.0).

In other embodiments provided by the invention, the compositions of blood glucose quality control liquid may include: 4 g polyethylene glycol 10000, 0.0003 g $NaN_3$, 200 mg/dL glucose, 500 mM NaCl, 100 mL 0.1 M phosphate buffer (pH=7.0).

In one embodiment of the blood glucose electrochemical test system provided by the invention, when the measured AC impedance angle value of the test sample is 9~22°, the test sample is judged as blood sample, when the measured AC impedance angle value of the test sample is 27~44°, the test sample is judged as blood glucose quality control liquid.

In another embodiment provided by the invention, the electrochemical test system may be uric acid electrochemical test system. In this embodiment, the quality control liquid is uric acid quality control liquid, the real sample is blood; and the process for judging the test sample as quality control liquid or real sample according to the AC impedance angle value includes: selecting an AC impedance angle threshold B to distinguish between the real sample and quality control liquid, and the threshold B is set as the 55%~65% of minimum value of AC impedance angle value for real sample, or the 200%~225% of maximum value of AC impedance angle value for quality control liquid;

When the measured AC impedance angle value of the test sample is larger than the threshold B, the test sample is judged as blood sample, when the measured AC impedance angle value of the test sample is smaller than the threshold B, the test sample is judged as quality control liquid. Although, in other embodiments, the case may be reversed.

The uric acid quality control liquid is composed of thickener, preservative, uric acid and buffer. In one embodiment, the concentration of thickener may be 0.08~0.14 g/mL, and in a particular embodiment, the concentration of thickener may be 0.12 g/mL. Preferably, the uric acid quality control liquid may be composed of polyethylene glycol 10000, $NaN_3$, uric acid and 0.1 M phosphate buffer (pH=7.0). In a particular embodiment, the concentration of polyethylene glycol 10000 may be 0.08~0.14 g/mL and in a particular embodiment, the concentration of polyethylene glycol 10000 may be 0.12 g/mL. More preferably, the compositions of uric acid quality control liquid include: 8-14 g polyethylene glycol 10000, 0.0003 g $NaN_3$, 500 μM uric acid, 100 mL 0.1 M phosphate buffer (pH=7.0).

In the embodiments provided by the invention, the compositions of uric acid quality control liquid may include: 12 g polyethylene glycol 10000, 0.0003 g $NaN_3$, 500 μM uric acid, 100 mL 0.1 M phosphate buffer (pH=7.0).

In the uric acid electrochemical test system provided by the invention, when the measured AC impedance angle value of the test sample is 13~29°, the test sample is judged as blood sample, when the measured AC impedance angle value of the test sample is 3~9°, the test sample is judged as uric acid quality control liquid.

In a particular embodiment, the AC impedance amplitude is 0.2~0.3V, the AC impedance frequency is 0.5~1.5 KHz. In an embodiment provided by the invention, the AC impedance amplitude is 0.25V, the AC impedance frequency is 1 KHz.

In the present invention, the reagents and instruments used in the method for distinguishing between the quality control liquid and the real sample in the electrochemical test system can be purchased from the market.

The following examples illustrate the effectiveness of the method presented in this invention by applying the method in several test systems for identifying quality control liquid and blood sample.

Example 1

Method to Distinguish Between Blood Glucose Quality Control Liquid and Blood During Blood Glucose Test The first example of the present invention is to increase the AC impedance angle value of blood glucose quality control liquid to automatically distinguish between blood glucose quality control liquid and blood.

Figure 1:
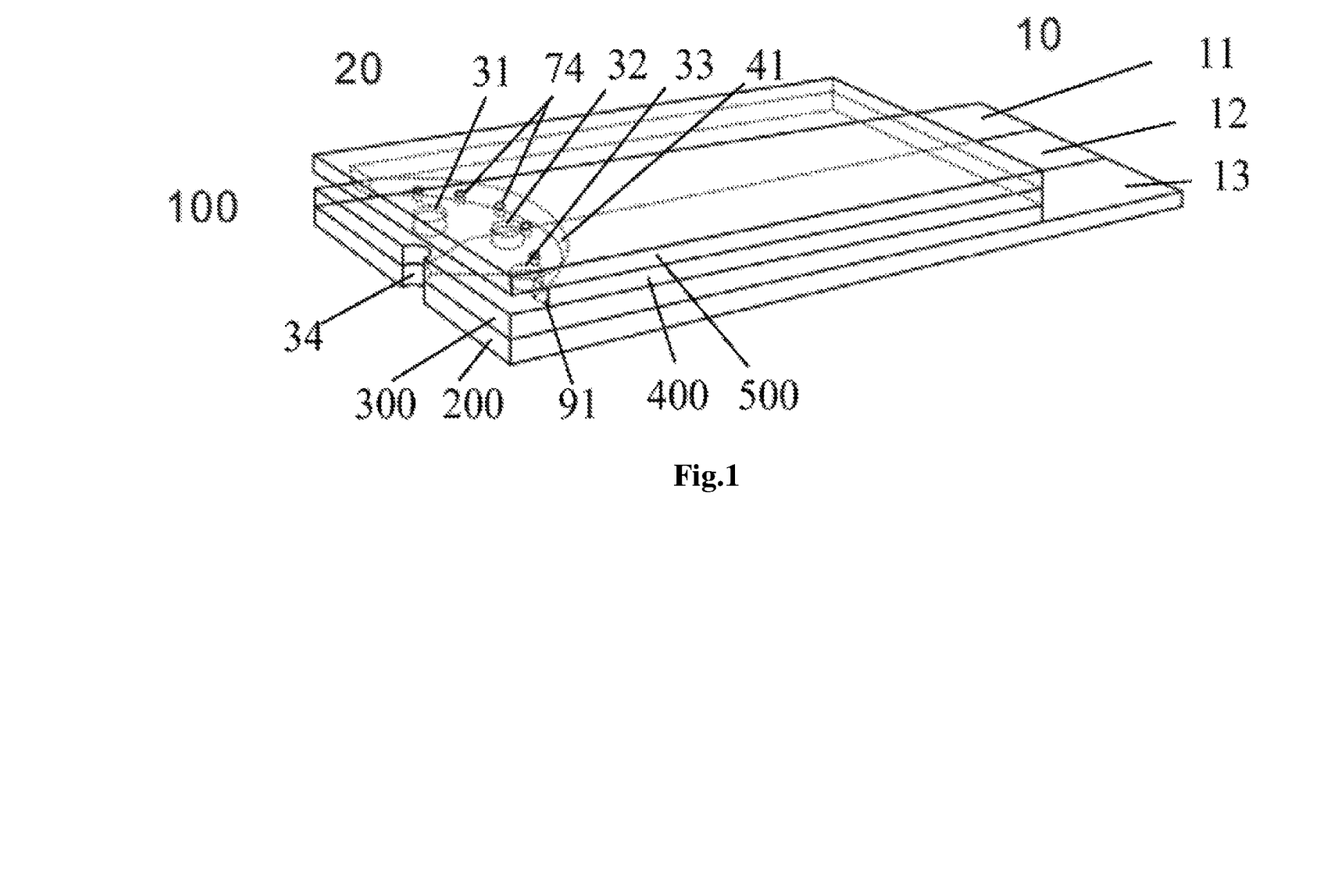
FIG. 1 is a schematic diagram of a test strip used in the invention.

FIG. 1 is a schematic diagram of an exemplary test strip used in the blood glucose test system. The test strip has a sensor body 100 with the electrodes located in the body 100. The two ends of the body 100 are an electric contact end 10 and sampling end 20, respectively. Sampling end 20 has a fluid chamber for receiving fluid sample. Both sides of the sampling end 20 (i.e. the side entrance 91) and the front side ("the front" is the end face of sampling end 20 in the sensor body 100) connect with the fluid chamber, respectively. The bottom of sampling end 20 has a notch 34 connecting with the fluid chamber.

Figure 2:
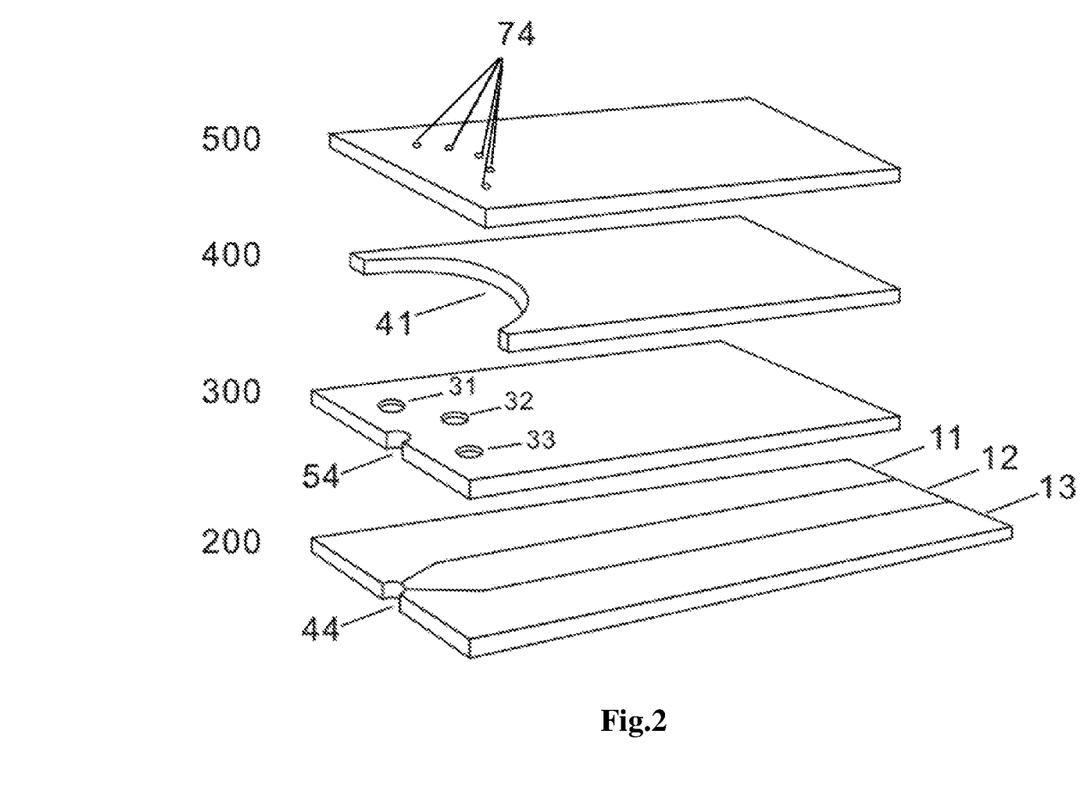
FIG. 2 is an exploded view of the structure showing the four layers of the test strip used in the invention.

FIG. 2 is an exploded view of the structure of the test strip used in the blood glucose test system. The test strip consists of multiple layers which include a first base layer 200; a second base layer 300; a first upper layer 400; and a second upper layer 500. The first base layer 200 made of insulating material has conductive coating on the surface. The conductive surface is separated into three conduits 11, 12, 13. The separate three conductive conduits terminate and are exposed for making an electric connection to a reading device at the end 10 opposite the sampling end 20 of the laminated body. The first base layer 200 also has a notch 44 at the front end of the sampling end 20. The second base layer 300 is made of insulating material having three cutouts 31, 32, 33 at the sampling end 20 and a notch 54 at the front end of the sampling end 20. One of the three round cutouts (31, 32, 33) corresponds to one of the three conduits (11, 12, 13) at the first base layer 200, and the three round cutouts (31, 32, 33) service as a working electrode 31; a first reference electrode 32 and a second reference electrode 33. The first upper layer 400 is also made of insulating material and has a semi-circular shaped cutout 41 at the sampling end 20. The second upper layer 500 is still made of insulating material and has several small openings 74 at the sampling end 20. The second upper layer 500 has one side coated with hydrophilic layer which faces the fluid chamber.

The working electrode 31 of this embodiment may be located with glucose oxidase, oxidative electron mediators (e.g. potassium ferricyanide), surfactant (e.g. Triton-100), polymer adhesive promoter (e.g. hydroxyethyl cellulose), fillers (e.g. lactose) and solvent, as shown in Table 1. Both reference electrode 32 and reference electrode 33 may be located with oxidative electron mediators (e.g. potassium ferricyanide), surfactant (e.g. Triton-100), polymer adhesive promoter (e.g. hydroxyethyl cellulose), fillers (e.g. lactose) and solvent, as shown in Table 2. In addition, the compositions of blood glucose quality control liquid used in the example is shown in Table 3.

After connecting the electrochemical test strip with the measuring instrument, supplying blood glucose quality control liquid or blood sample to the electrochemical test strip, then the AC impedance voltage signal is applied at a certain time. The AC impedance amplitude and frequency are 0.25 V and 1 KHz, respectively. Measuring the AC impedance angle values between working electrode 31 and reference electrode 32 (or reference electrode 33), taking the average AC impedance angle value of the twice measured values.

Figure 3:
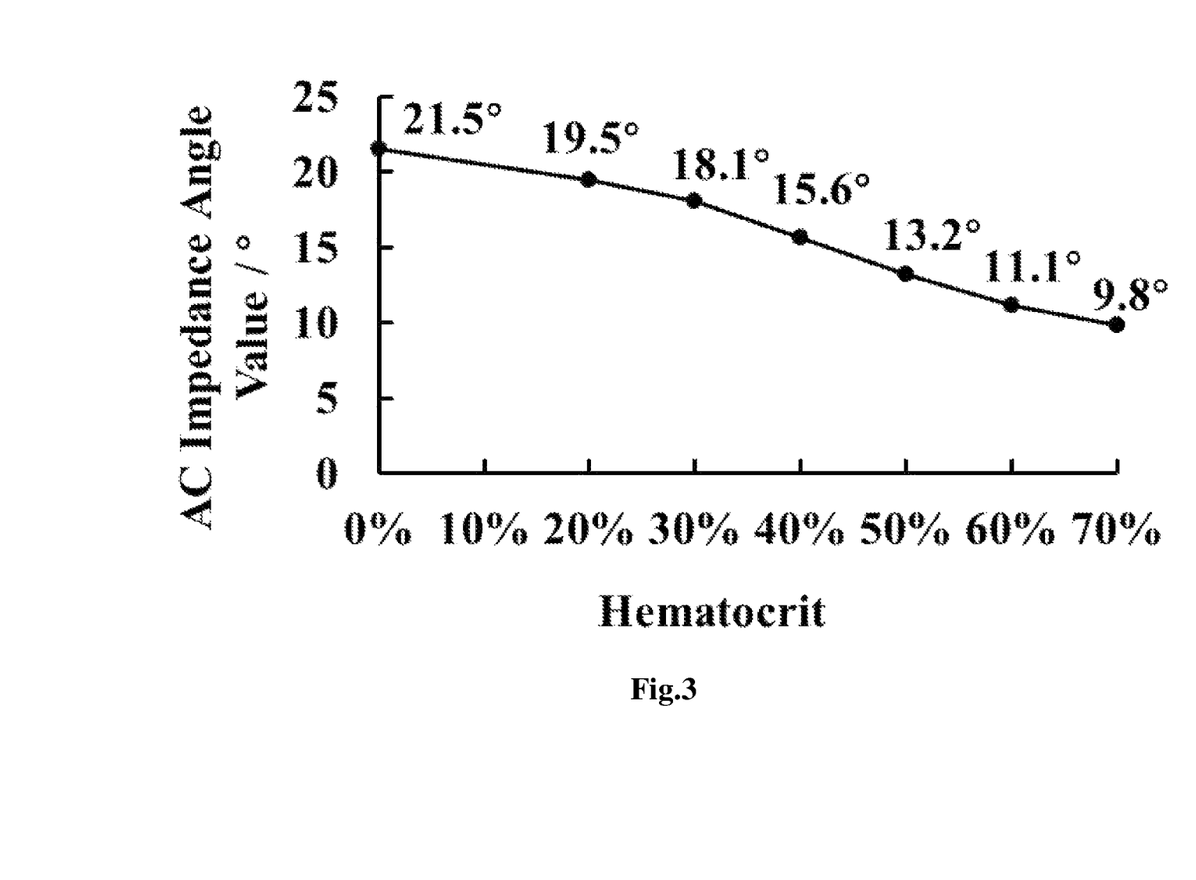
FIG. 3 shows the AC impedance angle values of blood samples with different hematocrits measured by the blood glucose test system in Example 1 provided by the invention.

FIG. 3 shows the AC impedance angle values of blood samples with different hematocrits measured by the blood glucose test system.

From the results shown in FIG. 3, when the hematocrit increases from 0% (plasma) to 70%, the measured AC impedance angle value decreases from 21.5° to 9.8°. However, the measured AC impedance angle value of the blood glucose quality control liquid shown in Table 3 is 35.3°, larger than that of blood sample. So the AC impedance angle value can be used to automatically distinguish between blood glucose quality control liquid and blood sample with hematocrit from 0% to 70%.

In addition, as discovered in this invention, varying the concentration of NaCl in the blood glucose quality control liquid can regulate the measured AC impedance angle value. Table 4 shows the measured AC impedance angle values of blood glucose quality control liquid with different concentrations of NaCl. When the concentration of NaCl is 100 mM, the measured AC impedance angle value for blood glucose control liquid is 22°, closed to the AC impedance angle value of blood sample (plasma with 0% hematocrit), which can not obviously distinguish between blood glucose quality control liquid and blood sample. Increasing the concentration of NaCl in the blood glucose quality control liquid leads to markedly increase the AC impedance angle value. The AC impedance angle value is ca.27° for 300 mM NaCl, ca.35° for 500 mM NaCl, ca.43° for 700 mM NaCl. After increasing the concentration of NaCl in the blood glucose quality control liquid, the AC impedance angle value can be used to automatically distinguish between blood glucose quality control liquid and blood sample. However, due to the narrow linearity range of blood glucose quality control liquid at 700 mM NaCl, the optimized concentration of NaCl is 500 mM for blood glucose quality control liquid.

TABLE 1

Compositions of working electrode for blood glucose test system

| Component | | Content |
| --- | --- | --- |
| Enzyme | Glucose Oxidase | 1% |
| Adhesive | Hydroxyethyl Cellulose | 5% |
| Surfactant | Triton-100 | 0.2% |
| Electron Mediator | Potassium Ferricyanide | 3% |
| Filler | Lactose | 5% |
| Solvent | Water | 85.8% |

TABLE 2

Compositions of reference electrode for blood glucose test system

| Component | | Content |
| --- | --- | --- |
| Adhesive | Hydroxyethyl Cellulose | 5% |
| Surfactant | Triton-100 | 0.2% |
| Electron Mediator | Potassium Ferricyanide | 3% |
| Filler | Lactose | 5% |
| Solvent | Water | 86.8% |

TABLE 3

Compositions of blood glucose quality control liquid

| Component | | Content |
| --- | --- | --- |
| Thickener | Polyethylene Glycol 10000 | 4 g |

TABLE 3-continued

Compositions of blood glucose quality control liquid

| Component | | Content |
|---|---|---|
| Preservative | NaN$_3$ | 0.0003 g |
| Analyte | Glucose | 200 mg/dL |
| Electrolyte | NaCl | 500 mM |
| Buffer | 0.1M Phosphate Buffer (pH = 7.0) | 100 mL |

TABLE 4

The measured AC impedance angle values of blood glucose quality control liquid with different concentrations of NaCl

| Formula | | Component | | Concentration of NaCl | Concentration of Glucose | AC Impedance Angle Value |
|---|---|---|---|---|---|---|
| Formula One | Thickener | Polyethylene Glycol 10000 | 4 g | 100 mM | 100 mg/dL | 22.2° |
| | Preservative | NaN$_3$ | 0.0003 g | | 200 mg/dL | 22.4° |
| | Buffer | 0.1M Phosphate Buffer (pH = 7.0) | 100 mL | | 300 mg/dL | 22.6° |
| Formula Two | Thickener | Polyethylene Glycol 10000 | 4 g | 300 mM | 100 mg/dL | 27.1° |
| | Preservative | NaN$_3$ | 0.0003 g | | 200 mg/dL | 27.6° |
| | Buffer | 0.1M Phosphate Buffer (pH = 7.0) | 100 mL | | 300 mg/dL | 27.8° |
| Formula Three | Thickener | Polyethylene Glycol 10000 | 4 g | 500 mM | 100 mg/dL | 35.1° |
| | Preservative | NaN$_3$ | 0.0003 g | | 200 mg/dL | 35.3° |
| | Buffer | 0.1M Phosphate Buffer (pH = 7.0) | 100 mL | | 300 mg/dL | 35.6° |
| Formula Four | Thickener | Polyethylene Glycol 10000 | 4 g | 700 mM | 100 mg/dL | 43.2° |
| | Preservative | NaN$_3$ | 0.0003 g | | 200 mg/dL | 43.7° |
| | Buffer | 0.1M Phosphate Buffer (pH = 7.0) | 100 mL | | 300 mg/dL | 43.9° |

1. The Practical Application of the Above Method

According to the test results in the Example 1, the invention also designs a set of logic judgment algorithm to prove that the method proposed in Example 1 can be practically applied to accurately distinguish between the blood sample and blood glucose quality control liquid. The used blood glucose quality control liquid is formula three with three glucose levels shown in Table 4, and the AC impedance angle value for formula three shown in Table 4 is ca.35°. The maximum AC impedance angle value for blood sample is 21.5° (plasma with 0% hematocrit). During the practical application, an AC impedance angle threshold is selected as a cut-off point to distinguish between the blood sample and blood glucose quality control liquid, the AC impedance angle threshold is set as the 130%~140% of maximum value of AC impedance angle value for blood sample, or the 80%~85% of minimum value of AC impedance angle value for blood glucose quality control liquid. When the measured AC impedance angle value of the test sample is smaller than the threshold, the test sample is judged as blood sample, when the measured AC impedance angle value of the test sample is larger than the threshold, the test sample is judged as blood glucose quality control liquid, then the quality control is carried out in the measuring instrument. The invention selects one AC impedance angle threshold 28.5° as the cut-off point to distinguish between the blood sample and blood glucose quality control liquid, then 10 blood samples and 10 blood glucose quality samples were continuously measured, respectively. The test results are shown in Table 5 and Table 6. From the results in Table 5 and Table 6, the method proposed in Example 1 can be practically applied to accurately distinguish between the blood glucose quality control liquid and blood sample with hematocrit from 0% to 70%, without incorrect judgement.

TABLE 5

Identifying blood sample by blood glucose test system

| | Blood Sample | | | | | | | | | |
|---|---|---|---|---|---|---|---|---|---|---|
| | 1 | 2 | 3 | 4 | 5 | 6 | 7 | 8 | 9 | 10 |
| AC Impedance Angle Value/° | 15.6 | 18.9 | 11.6 | 19.1 | 10.9 | 13.7 | 12.4 | 18.1 | 19.8 | 14.2 |
| Whether Judged as Blood | Yes | Yes | Yes | Yes | Yes | Yes | Yes | Yes | Yes | Yes |

TABLE 6

Identifying blood glucose quality control liquid by blood glucose test system

| | Blood Glucose Quality Control Liquid Sample | | | | | | | | | |
|---|---|---|---|---|---|---|---|---|---|---|
| | 1 | 2 | 3 | 4 | 5 | 6 | 7 | 8 | 9 | 10 |
| AC Impedance Angle Value/° | 35.2 | 35.6 | 35.4 | 35.1 | 35.7 | 35.2 | 35.4 | 35.3 | 35.5 | 35.2 |
| Whether Judged as Control Liquid | Yes | Yes | Yes | Yes | Yes | Yes | Yes | Yes | Yes | Yes |

Example 2

Method to Distinguish Between Creatinine Quality Control Liquid and Blood During Creatinine Test The second example of the present invention is to increase the AC impedance angle value of creatinine quality control liquid to automatically distinguish between creatinine quality control liquid and blood.

The electrode structure used in the Example 2 of the invention may be the same as that in the Example 1. The working electrode 31 is located with creatininase, creatinase, sarcosine oxidase, peroxidase, reductive electron mediators (e.g. potassium ferrocyanide), surfactant (e.g. Triton-100), polymer adhesive promoter (e.g. hydroxyethyl cellulose), fillers (e.g. lactose) and solvent, as shown in Table 7.

Both reference electrode 32 and reference electrode 33 are located with creatinase, sarcosine oxidase, peroxidase, reductive electron mediators (e.g. potassium ferrocyanide), surfactant (e.g. Triton-100), polymer adhesive promoter (e.g. hydroxyethyl cellulose), fillers (e.g. lactose) and solvent, as shown in Table 8. In addition, the compositions of creatinine quality control liquid used in the example is shown in Table 9.

Figure 4:
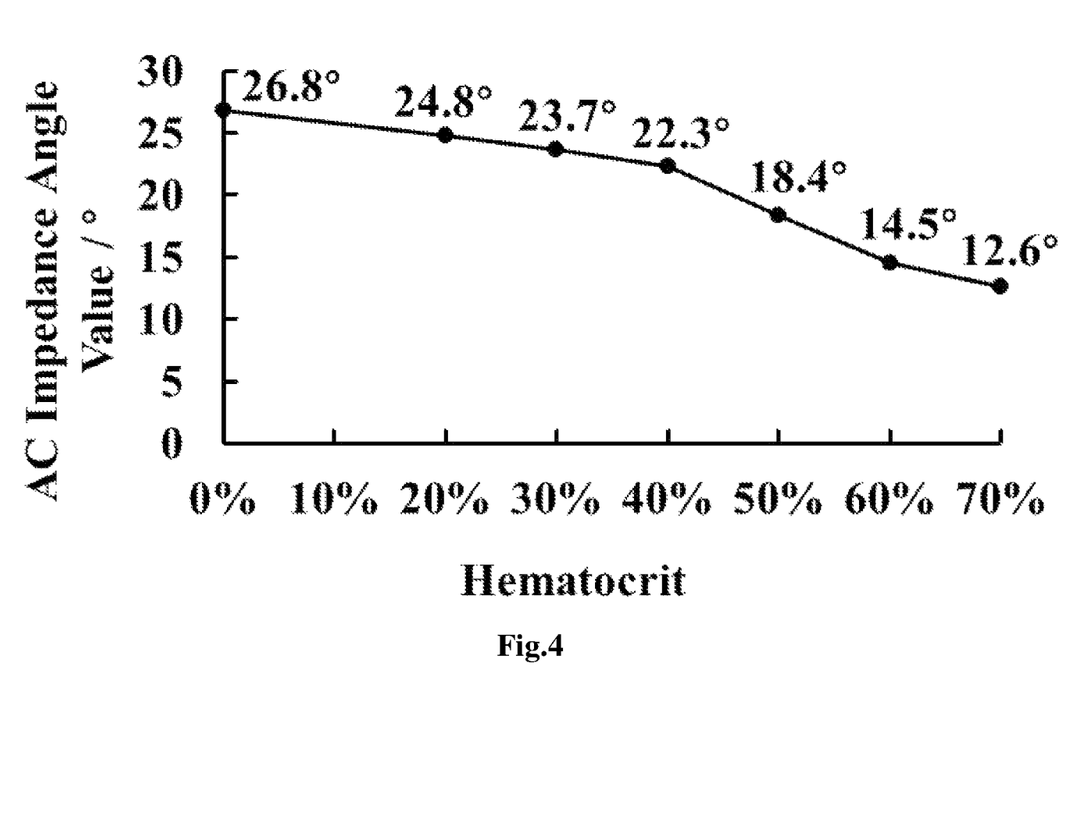
FIG. 4 shows the AC impedance angle values of blood samples with different hematocrits measured by the creatinine test system in Example 2 provided by the invention.

After connecting the electrochemical test strip with the measuring instrument, supplying creatinine quality control liquid or blood sample to the electrochemical test strip, then the AC impedance voltage signal is applied at a certain time. The AC impedance amplitude and frequency are 0.25 V and 1 KHz, respectively. Measuring the AC impedance angle values between working electrode 31 and reference electrode 32 (or reference electrode 33), taking the average AC impedance angle value of the twice measured values. FIG. 4 shows the AC impedance angle values of blood samples with different hematocrits measured by the creatinine test system.

From the results shown in FIG. 4, when the hematocrit increases from 0% (plasma) to 70%, the measured AC impedance angle value decreases from 26.8° to 12.6°. However, the measured AC impedance angle value of the creatinine quality control liquid shown in Table 9 is 43.2°, larger than that of blood sample. So the AC impedance angle value can be used to automatically distinguish between creatinine quality control liquid and blood sample with hematocrit from 0% to 70%.

In the same way, varying the concentration of NaCl in the creatinine quality control liquid can regulate the measured AC impedance angle value. Table 10 shows the measured AC impedance angle values of creatinine quality control liquid with different concentrations of NaCl. When the concentration of NaCl is 100 mM, the measured AC impedance angle value for creatinine quality control liquid is 27°, closed to the AC impedance angle value of blood sample (plasma with 0% hematocrit), which can not obviously distinguish between creatinine quality control liquid and blood sample. Increasing the concentration of NaCl in the creatinine quality control liquid leads to markedly increase the AC impedance angle value. The AC impedance angle value is ca.35° for 300 mM NaCl, ca.43° for 400 mM NaCl, ca.50° for 500 mM NaCl. After increasing the concentration of NaCl in the creatinine quality control liquid, the AC impedance angle value can be used to automatically distinguish between creatinine quality control liquid and blood sample. However, due to the narrow linearity range of creatinine quality control liquid at 500 mM NaCl, the optimized concentration of NaCl is 400 mM for creatinine quality control liquid.

TABLE 7

Compositions of working electrode for creatinine test system

| | Component | Content |
|---|---|---|
| Enzyme | Creatininase | 1.0% |
| Enzyme | Creatinase | 3.5% |
| Enzyme | Sarcosine Oxidase | 2.5% |
| Enzyme | Peroxidase | 1.0% |
| Adhesive | Hydroxyethyl Cellulose | 5% |
| Surfactant | Triton-100 | 0.2% |
| Electron Mediator | Potassium Ferrocyanide | 3% |
| Filler | Lactose | 5% |
| Solvent | Water | 78.8% |

TABLE 8

Compositions of reference electrode for creatinine test system

| Component | | Content |
|---|---|---|
| Enzyme | Creatinase | 3.5% |
| Enzyme | Sarcosine Oxidase | 2.5% |
| Enzyme | Peroxidase | 1.0% |
| Adhesive | Hydroxyethyl Cellulose | 5% |
| Surfactant | Triton-100 | 0.2% |
| Electron Mediator | Potassium Ferrocyanide | 3% |
| Filler | Lactose | 5% |
| Solvent | Water | 79.8% |

TABLE 9

Compositions of creatinine quality control liquid

| Component | | Content |
|---|---|---|
| Thickener | Polyethylene Glycol 10000 | 4 g |
| Preservative | $NaN_3$ | 0.0003 g |
| Analyte | Creatinine | 3 mg/dL |
| Electrolyte | NaCl | 400 mM |
| Buffer | 0.1M Phosphate Buffer (pH = 7.0) | 100 mL |

TABLE 10

The measured AC impedance angle values of creatinine quality control liquid with different concentrations of NaCl

| Formula | | Component | | Concentration of NaCl | Concentration of Creatinine | AC Impedance Angle Value |
|---|---|---|---|---|---|---|
| Formula One | Thickener | Polyethylene Glycol 10000 | 4 g | 100 mM | 1 mg/dL | 26.7° |
| | Preservative | $NaN_3$ | 0.0003 g | | 3 mg/dL | 26.8° |
| | Buffer | 0.1M Phosphate Buffer (pH = 7.0) | 100 mL | | 5 mg/dL | 26.9° |
| Formula Two | Thickener | Polyethylene Glycol 10000 | 4 g | 300 mM | 1 mg/dL | 35.5° |
| | Preservative | $NaN_3$ | 0.0003 g | | 3 mg/dL | 35.6° |
| | Buffer | 0.1M Phosphate Buffer (pH = 7.0) | 100 mL | | 5 mg/dL | 35.8° |
| Formula Three | Thickener | Polyethylene Glycol 10000 | 4 g | 400 mM | 1 mg/dL | 43.1° |
| | Preservative | $NaN_3$ | 0.0003 g | | 3 mg/dL | 43.2° |
| | Buffer | 0.1M Phosphate Buffer (pH = 7.0) | 100 mL | | 5 mg/dL | 43.4° |
| Formula Four | Thickener | Polyethylene Glycol 10000 | 4 g | 500 mM | 1 mg/dL | 50.2° |
| | Preservative | $NaN_3$ | 0.0003 g | | 3 mg/dL | 50.3° |
| | Buffer | 0.1M Phosphate Buffer (pH = 7.0) | 100 mL | | 5 mg/dL | 50.5° |

The Practical Application of the Above Method

According to the test results in the Example 2, the invention also designs a set of logic judgment algorithm to prove that the method proposed in Example 2 can be practically applied to accurately distinguish between the blood sample and creatinine quality control liquid. The used creatinine quality control liquid is formula three with three creatinine levels shown in Table 10, and the AC impedance angle value for formula three shown in Table 10 is ca.43°. The maximum AC impedance angle value for blood sample is 26.8° (plasma with 0% hematocrit). During the practical application, an AC impedance angle threshold is selected as a cut-off point to distinguish between the blood sample and creatinine quality control liquid, the AC impedance angle threshold is set as the 130%~140% of maximum value of AC impedance angle value for blood sample, or the 80%~85% of minimum value of AC impedance angle value for creatinine quality control liquid. When the measured AC impedance angle value of the test sample is smaller than the threshold, the test sample is judged as blood sample, when the measured AC impedance angle value of the test sample is larger than the threshold, the test sample is judged as creatinine quality control liquid, then the quality control is carried out in the measuring instrument. The invention selects one AC impedance angle threshold 35.2° as the cut-off point to distinguish between the blood sample and creatinine quality control liquid, then 10 blood samples and 10 creatinine quality control liquid samples were continuously measured, respectively. The test results are shown in Table 11 and Table 12. From the results in Table 11 and Table 12, the method proposed in Example 2 can be practically applied to accurately distinguish between the creatinine quality control liquid and blood sample with hematocrit from 0% to 70%, without incorrect judgement.

TABLE 11

Identifying blood sample by creatinine test system

| | Blood Sample | | | | | | | | | |
|---|---|---|---|---|---|---|---|---|---|---|
| | 1 | 2 | 3 | 4 | 5 | 6 | 7 | 8 | 9 | 10 |
| AC Impedance Angle Value/° | 13.2 | 15.8 | 22.5 | 25.8 | 18.7 | 17.5 | 19.5 | 20.4 | 13.9 | 16.1 |
| Whether Judged as Blood | Yes | Yes | Yes | Yes | Yes | Yes | Yes | Yes | Yes | Yes |

TABLE 12

Identifying creatinine quality control liquid by creatinine test system

| | Creatinine Quality Control Liquid Sample | | | | | | | | | |
|---|---|---|---|---|---|---|---|---|---|---|
| | 1 | 2 | 3 | 4 | 5 | 6 | 7 | 8 | 9 | 10 |
| AC Impedance Angle Value/° | 43.1 | 43.2 | 43.2 | 43.1 | 43.2 | 43.1 | 43.5 | 43.2 | 43.3 | 43.4 |
| Whether Judged as Control Liquid | Yes | Yes | Yes | Yes | Yes | Yes | Yes | Yes | Yes | Yes |

Example 3

Method to Distinguish Between Uric Acid Quality Control Liquid and Blood During Uric Acid Test The third example of the present invention is to decrease the AC impedance angle value of uric acid quality control liquid to automatically distinguish between uric acid quality control liquid and blood.

The electrode structure used in the Example 3 of the invention may be the same as that in the Example 1. The working electrode 31 is located with uricase, peroxidase, reductive electron mediators (e.g. potassium ferrocyanide), surfactant (e.g. Triton-100), polymer adhesive promoter (e.g. hydroxyethyl cellulose), fillers (e.g. lactose) and solvent, as shown in Table 13.

Both reference electrode 32 and reference electrode 33 are located with reductive electron mediators (e.g. potassium ferrocyanide), surfactant (e.g. Triton-100), polymer adhesive promoter (e.g. hydroxyethyl cellulose), fillers (e.g. lactose) and solvent, as shown in Table 14.

In addition, the compositions of uric acid quality control liquid used in the example is shown in Table 15.

Figure 5:
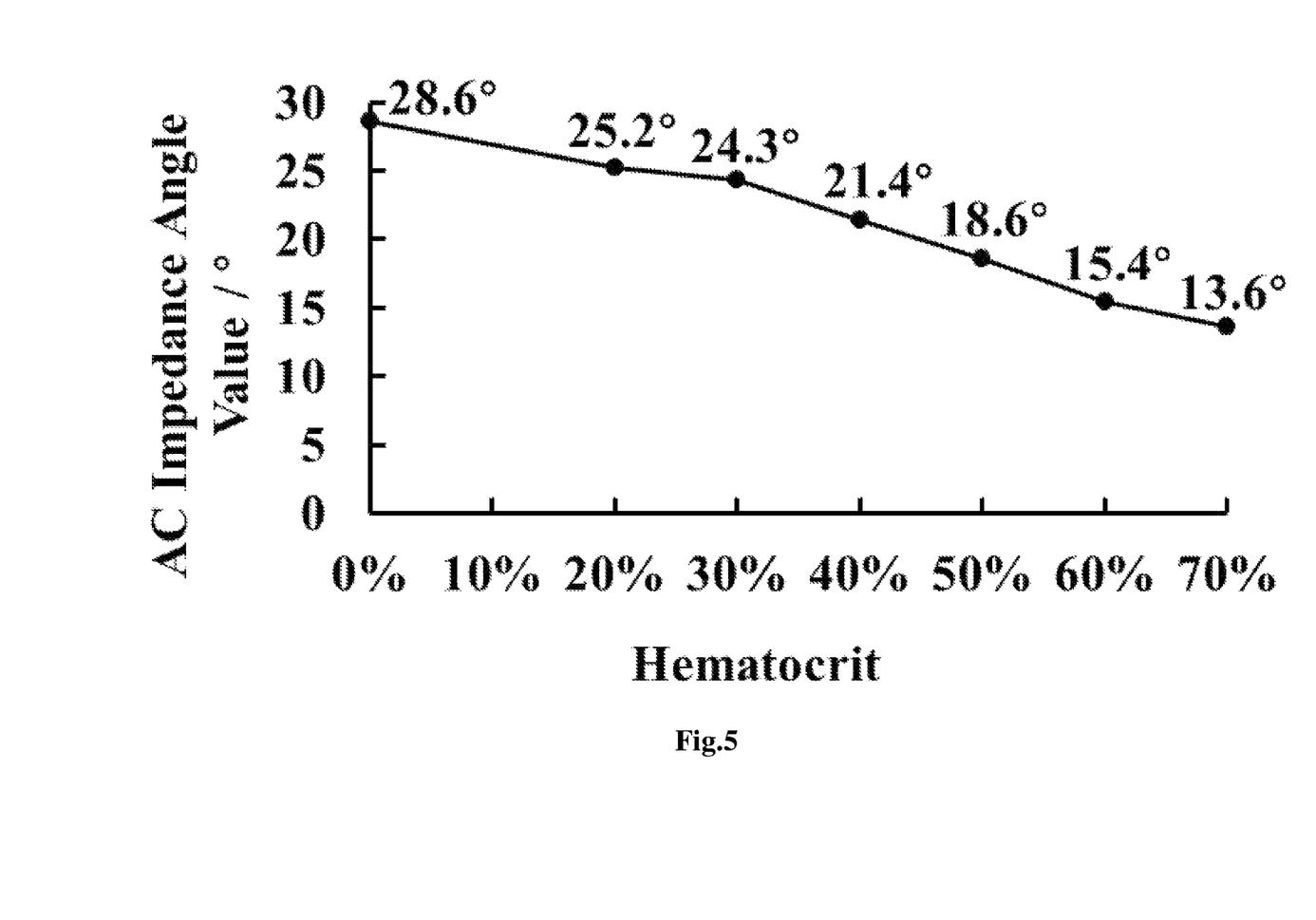
FIG. 5 shows the AC impedance angle values of blood samples with different hematocrits measured by the uric acid test system in Example 3 provided by the invention.

After connecting the electrochemical test strip with the measuring instrument, supplying uric acid quality control liquid or blood sample to the electrochemical test strip, then the AC impedance voltage signal is applied at a certain time. The AC impedance amplitude and frequency are 0.25 V and 1 KHz, respectively. Measuring the AC impedance angle values between working electrode 31 and reference electrode 32 (or reference electrode 33), taking the average AC impedance angle value of the twice measured values. FIG. 5 shows the AC impedance angle values of blood samples with different hematocrits measured by the uric acid test system.

From the results shown in FIG. 5, when the hematocrit increases from 0% (plasma) to 70%, the measured AC impedance angle value decreases from 28.6° to 13.6°. However, the measured AC impedance angle value of the uric acid quality control liquid shown in Table 15 is 4.2°, smaller than that of blood sample. So the AC impedance angle value can be used to automatically distinguish between uric acid quality control liquid and blood sample with hematocrit from 0% to 70%.

In addition, as discovered in this invention, varying the content of polyethylene glycol 10000 in the uric acid quality control liquid can regulate the measured AC impedance angle value. Table 16 shows the measured AC impedance angle values of uric acid quality control liquid with different contents of polyethylene glycol 10000. When the content of polyethylene glycol 10000 is 5 g, the measured AC impedance angle value for uric acid quality control liquid is 12°, closed to the AC impedance angle value of blood sample (70% hematocrit), which can not obviously distinguish between uric acid quality control liquid and blood sample. Increasing the content of polyethylene glycol 10000 in the uric acid quality control liquid leads to markedly decrease the AC impedance angle value. The AC impedance angle value is ca.8° for 8 g polyethylene glycol 10000, ca.4° for 12 g polyethylene glycol 10000, ca.3° for 14 g polyethylene glycol 10000. After increasing the content of polyethylene glycol 10000 in the uric acid quality control liquid, the AC impedance angle value can be used to automatically distinguish between uric acid quality control liquid and blood sample. However, due to the narrow linearity range of uric acid quality control liquid at 14 g polyethylene glycol 10000, the optimized content of polyethylene glycol 10000 is 12 g for uric acid quality control liquid.

TABLE 13

Compositions of working electrode for uric acid test system

| | Component | Content |
|---|---|---|
| Enzyme | Uricase | 0.5% |
| Enzyme | Peroxidase | 0.5% |

TABLE 13-continued

Compositions of working electrode for uric acid test system

| Component | | Content |
|---|---|---|
| Adhesive | Hydroxyethyl Cellulose | 5% |
| Surfactant | Triton-100 | 0.2% |
| Electron Mediator | Potassium Ferrocyanide | 3% |
| Filler | Lactose | 5% |
| Solvent | Water | 85.8% |

TABLE 14

Compositions of reference electrode for uric acid test system

| Component | | Content |
|---|---|---|
| Adhesive | Hydroxyethyl Cellulose | 5% |
| Surfactant | Triton-100 | 0.2% |
| Electron Mediator | Potassium Ferrocyanide | 3% |
| Filler | Lactose | 5% |
| Solvent | Water | 86.8% |

TABLE 15

Compositions of uric acid quality control liquid

| Component | | Content |
|---|---|---|
| Thickener | polyethylene glycol 10000 | 12 g |
| Preservative | NaN$_3$ | 0.0003 g |
| Analyte | Uric Acid | 500 μM |
| Buffer | 0.1M Phosphate Buffer (pH = 7.0) | 100 mL |

TABLE 16

The measured AC impedance angle values of uric acid quality control liquid with different content of polyethylene glycol 10000

| Formula | Component | | | Content of Polyethylene Glycol 10000 | Concentration of Uric Acid | AC Impedance Angle Value |
|---|---|---|---|---|---|---|
| Formula One | Preservative | NaN$_3$ | 0.0003 g | 5 g | 200 μM | 12.1° |
| | | | | | 500 μM | 12.4° |
| | Buffer | 0.1M Phosphate Buffer (pH = 7.0) | 100 mL | | 800 μM | 12.5° |
| Formula Two | Preservative | NaN$_3$ | 0.0003 g | 8 g | 200 μM | 8.2° |
| | | | | | 500 μM | 8.4° |
| | Buffer | 0.1M Phosphate Buffer (pH = 7.0) | 100 mL | | 800 μM | 8.5° |
| Formula Three | Preservative | NaN$_3$ | 0.0003 g | 12 g | 200 μM | 4.1° |
| | | | | | 500 μM | 4.2° |
| | Buffer | 0.1M Phosphate Buffer (pH = 7.0) | 100 mL | | 800 μM | 4.5° |
| Formula Four | Preservative | NaN$_3$ | 0.0003 g | 14 g | 200 μM | 3.2° |
| | | | | | 500 μM | 3.4° |
| | Buffer | 0.1M Phosphate Buffer (pH = 7.0) | 100 mL | | 800 μM | 3.5° |

The Practical Application of the Above Method

According to the test results in the Example 3, the invention also designs a set of logic judgment algorithm to prove that the method proposed in Example 3 can be practically applied to accurately distinguish between the blood sample and uric acid quality control liquid. The used uric acid quality control liquid is formula three with three creatinine levels shown in Table 16, and the AC impedance angle value for formula three shown in Table 16 is ca. 4°, the minimum AC impedance angle value for blood sample is 13.6° (70% hematocrit). During the practical application, an AC impedance angle threshold is selected as a cut-off point to distinguish between the blood sample and uric acid quality control liquid, the AC impedance angle threshold is set as the 55%~65% of minimum value of AC impedance angle value for blood sample, or the 200%~225% of maximum value of AC impedance angle value for uric acid quality control liquid. When the measured AC impedance angle value of the test sample is larger than the threshold, the test sample is judged as blood sample, when the measured AC impedance angle value of the test sample is smaller than the threshold, the test sample is judged as uric acid quality control liquid, then the quality control is carried out in the measuring instrument. The invention selects one AC impedance angle threshold 8.4° as the cut-off point to distinguish between the blood sample and uric acid quality control liquid, then 10 blood samples and 10 uric acid quality control liquid samples were continuously measured, respectively. The test results are shown in Table 17 and Table 18. From the results in Table 17 and Table 18, the method proposed in Example 3 can be practically applied to accurately distinguish between the uric acid quality control liquid and blood sample with hematocrit from 0% to 70%, without incorrect judgement.

TABLE 17

Identifying blood sample by uric acid test system

| | Blood Sample | | | | | | | | | |
|---|---|---|---|---|---|---|---|---|---|---|
| | 1 | 2 | 3 | 4 | 5 | 6 | 7 | 8 | 9 | 10 |
| AC Impedance Angle Value/° | 25.4 | 20.8 | 17.6 | 19.5 | 18.4 | 21.6 | 14.6 | 15.9 | 21.3 | 16.2 |
| Whether Judged as Blood | Yes | Yes | Yes | Yes | Yes | Yes | Yes | Yes | Yes | Yes |

TABLE 18

Identifying uric acid quality control liquid by uric acid test system

| | Uric Acid Quality Control Liquid Sample | | | | | | | | | |
|---|---|---|---|---|---|---|---|---|---|---|
| | 1 | 2 | 3 | 4 | 5 | 6 | 7 | 8 | 9 | 10 |
| AC Impedance Angle Value/° | 4.3 | 4.6 | 4.2 | 4.1 | 4.5 | 4.6 | 4.5 | 4.3 | 4.4 | 4.2 |
| Whether Judged as Control Liquid | Yes | Yes | Yes | Yes | Yes | Yes | Yes | Yes | Yes | Yes |

It should be noted that although the particular embodiments of the present invention have been described herein, the above description is merely for illustration purpose. Further modification and variations of the invention herein disclosed will occur to those skilled in the respective arts and all such modifications and variations are deemed to be within the scope of the invention as defined by the appended claims.

What is claimed is:

1. An electrochemical test system capable of determining if a fluid is one of a quality control liquid and a test sample comprising:
   an electrochemical test strip configured to receive a fluid, the fluid being one of the quality control liquid and the test sample;
   a measuring instrument, the electrochemical test strip in electronic communication with the measuring instrument, wherein the measuring instrument is operable to:
   apply an AC voltage signal to an electrode of the electrochemical test strip;
   measure an AC impedance angle value when the fluid is received in a sample chamber of the electrochemical test strip;
   determine if the fluid is the quality control liquid or the test sample based only on the measured AC impedance angle value;
   wherein the measuring instrument comprises a computerized device having a stored predetermined AC impedance angle value threshold, and the measuring instrument is configured to determine if the one of the fluid is the quality control liquid or the test sample by comparing the measured AC impedance angle value to the predetermined AC impedance angle value threshold and identifying if the measured AC impedance angle value is greater than or less than the predetermined AC impedance angle value threshold.

2. The electrochemical test system of claim 1 wherein the measuring instrument is operable to determine that the fluid is the test sample when the measured AC impedance angle value is greater than the predetermined AC impedance angle value threshold.

3. The electrochemical test system of claim 1 wherein the measuring instrument is operable to determine that the fluid is the test sample when the measured AC impedance angle value is less than the predetermined AC impedance angle value threshold.

4. The electrochemical test system of claim 1 wherein the predetermined AC impedance angle value threshold is set as approximately 130%-140% of a maximum expected AC impedance angle value for the test sample.

5. The electrochemical test system of claim 1 wherein the predetermined AC impedance angle value threshold is set as approximately 80%-85% of a minimum expected AC impedance angle value for the quality control liquid.

6. The electrochemical test system of claim 1 wherein the predetermined AC impedance angle value threshold is set as approximately 55-65% of a minimum expected AC impedance angle value for the test sample.

7. The electrochemical test system of claim 1 wherein the predetermined AC impedance angle value threshold is set as approximately 200%-225% of a maximum expected AC impedance angle value for the quality control liquid.

8. The electrochemical test system of claim 1 wherein the electrochemical test sensor is configured to measure creatinine, wherein the predetermined AC impedance angle value threshold is approximately 35.2°, and wherein the measuring instrument is configured to determine that the fluid is the test sample which is a blood sample when the measured AC impedance angle value is below approximately 35.2°, and configured to determine that the fluid is the quality control liquid when the measured AC impedance angle value is above approximately 35.2°.

9. The electrochemical test system of claim 1 wherein the electrochemical test strip is configured to measure blood glucose, and wherein measuring instrument is configured to determine that the fluid is the test sample which is a blood sample when the measured AC impedance angle value is between approximately 9-22°.

10. The electrochemical test system of claim 1 wherein the electrochemical test strip is configured to measure blood glucose, and wherein the measuring instrument is configured to determine that the fluid is the quality control liquid which is a blood glucose quality control liquid when the measured AC impedance angle value is between approximately 27-44°.

11. The electrochemical test system of claim 1 wherein the electrochemical test strip is configured to measure uric acid, and wherein measuring instrument is configured to determine that the fluid is the test sample which is a blood sample when the measured AC impedance angle value is between approximately 13-29°.

12. The electrochemical test system of claim 1 wherein the electrochemical test strip is configured to measure uric acid, and wherein the measuring instrument is configured to determine that the fluid is the quality control liquid which is a uric acid quality control liquid when the measured AC impedance angle value is between approximately 3-9°.

13. The electrochemical test system of claim 1 wherein the measuring instrument is configured to measure the AC impedance angle value between a working electrode and a reference electrode of the electrochemical test strip.

14. The electrochemical test system of claim 1 wherein the quality control fluid comprises an electrolyte in a concentration greater than 100 mM.

15. The electrochemical test system of claim 1 wherein the measuring instrument is configured to apply the AC voltage signal having an AC impedance amplitude of approximately 0.25V; and
    wherein the measuring instrument is configured to apply the AC voltage signal having an AC impedance frequency of approximately 1 KHz.

16. The electrochemical test system of claim 1 wherein the measuring instrument having a plurality of stored predetermined AC impedance angle value thresholds;
    wherein the measuring instrument is operable to identify a code of the electrochemical test strip, the code corresponding to a type of the electrochemical test strip; and
    wherein the measuring instrument is configured to select one of the plurality of AC impedance angle value thresholds based on the identified code of electrochemical test strip for comparing the measured AC impedance angle value to the predetermined AC impedance angle value threshold.

17. A method of automatically determining if a fluid is a test sample or a quality control liquid using an electrochemical test system comprising the steps of:
    connecting an electrochemical test strip to a measuring instrument, the electrochemical test strip having a working electrode and a reference electrode;
    drawing the fluid into a test chamber of the electrochemical test strip;
    applying an AC voltage signal to at least one electrode of the electrochemical test strip;
    measuring only an AC impedance angle value between the working electrode and the reference electrode; and
    determining, by the measuring instrument, if the fluid is the test sample or the quality control liquid by comparing the measured AC impedance angle value to a predetermined AC impedance angle value threshold and identifying if the measured AC impedance angle value is greater than or less than the predetermined AC impedance angle value threshold.

18. The method of claim 17 wherein the step of determining if the fluid is the test sample or the quality control sample comprises identifying if the measured AC impedance angle value is within a first range, the first range corresponding to the test sample; and identifying if the measured AC impedance angle value is within a second range, the second range corresponding to the quality control liquid.

* * * * *